United States Patent [19]

Gitelis

[11] Patent Number: 5,147,403
[45] Date of Patent: Sep. 15, 1992

[54] PROSTHESIS IMPLANTATION METHOD

[75] Inventor: Steven Gitelis, Oakbrook, Ill.

[73] Assignee: United States Gypsum Company, Chicago, Ill.

[21] Appl. No.: 324,208

[22] Filed: Mar. 15, 1989

[51] Int. Cl.$^5$ .............................................. A61F 2/28
[52] U.S. Cl. ........................................ 623/16; 623/66
[58] Field of Search .................... 523/116, 113–115; 623/16, 66

[56] References Cited

U.S. PATENT DOCUMENTS

| | | |
|---|---|---|
| 3,233,082 | 12/1965 | Smith . |
| 3,304,189 | 2/1967 | Kuntze . |
| 3,393,116 | 7/1968 | Larson . |
| 3,573,947 | 4/1971 | Kinkade . |
| 3,605,123 | 9/1971 | Hahn . |
| 3,885,638 | 12/1974 | Pilliar . |
| 4,059,456 | 11/1977 | DeRooy . |
| 4,169,747 | 10/1979 | DeRooy . |
| 4,184,887 | 1/1980 | Lange . |
| 4,309,488 | 1/1982 | Heide . |
| 4,356,572 | 11/1982 | Guillemin . |
| 4,360,386 | 11/1982 | Bounini . |
| 4,373,217 | 2/1983 | Draenert . |
| 4,435,183 | 3/1984 | Baehr . |
| 4,550,448 | 11/1985 | Kenna . |
| 4,619,655 | 10/1986 | Hanker et al. ................ 623/1 |

FOREIGN PATENT DOCUMENTS

WO87/05521  9/1987  PCT Int'l Appl. .

OTHER PUBLICATIONS

"Antibiotic-Impregnated Gypsum Pellets in the Surgical Management of Chronic Osteomyelitis," *International Medicine Supp. No. 9*, pp. 7–9, Mackey.

"Antibiotic Loaded Plaster of Paris Pellets," Clinical Orthopedic and Related Reseach, 167, 263–268, (1982), Mackey.

"Setting of Composite Hydroxylapatite/Plaster Implants With Blood for Bone Reconstruction," *Proc. 44th Annual Meeting 9th Electron Microscopy Soc. of Am.*, pp. 328–329, Hanker et al., 1986.

"Repair of Cortical Defects With A Partially Absorbable Hydroxylaptite Based Composite," 13th Annual Meeting of the Society of Biomaterials, Parsons, et al., Jun., 1987.

"Filling of Fresh Tooth Root Extraction Sites With An Hydroxylaptite Based Composite," 13th Annual Meeting of the Society of Biomaterials, Ricci, et al, Jun., 1987.

"Evaluation in cats of a material for cranioplasty: A composite of plaster of paris and hydroxylapatite," Rawlings, et al.

*Primary Examiner*—David Isabella
*Assistant Examiner*—G. Gualtieri
*Attorney, Agent, or Firm*—Willian Brnks Olds Hofer Gilson & Lione

[57] ABSTRACT

A technique for implanting a prosthesis is provided. According to the technique a prosthesis is implanted in a host bone by preparing the surface of the host bone to receive the prosthesis, applying calcium sulfate in free-flowing form to the receiving surface of the host bone, and seating the prosthesis in the receiving surface, whereby the calcium sulfate fills one or more gaps resulting between the prosthesis and the host bone.

9 Claims, No Drawings

PROSTHESIS IMPLANTATION METHOD

BACKGROUND OF THE INVENTION

The present invention relates generally to a technique for implanting a prosthesis and more particularly to a technique for implanting a prosthesis of the "cementless" type.

Since the development of the first cemented hip arthroplasty during the 1960s, cemented prosthesis arthroplasty has remained a successful orthopedic procedure for the treatment of arthritis and other afflictions of joints. The fixation of early devices was achieved by using methyl methacrylate which is a polymer created by mixing a powder and liquid. After mixing, the methyl methacrylate goes through several phases until it achieves a hardened state. Initially the material is free-flowing, then becomes doughy, and finally the material hardens at the conclusion of the polymerization process. The polymerization of methyl methacrylate is an exothermic reaction reaching a temperature of approximately 54° C.

Methyl methacrylate, also known as bone cement, has no bonding properties. It simply acts as a non-bioabsorbable spacer that fills the bone cavity, thus providing for prosthesis fixation. The problem with cemented arthroplasty is the lack of long term durability. There is a significant incidence of loosening of these devices caused by failure at the bone cement interface. This is especially true when these devices are implanted in younger patients. This failure rate has spurned an interest in cementless prosthesis arthroplasty.

Another problem arises because the polymerization of methyl methacrylate is an exothermic reaction. The reaction itself destroys some of the tissue surrounding the prosthesis.

Cementless prosthesis technology was developed during the 1970's and 80's, and consists of implantation of devices that have a porous surface. Such prostheses are disclosed, for example, in U.S. Pat. No. 3,605,123 (Hahn), which is incorporated herein by reference. The prosthesis disclosed in this reference includes a dense metal base and an overlying highly porous metallic layer which permits growth of bone tissue into the pores. Other cementless prostheses are disclosed in U.S. Pat. Nos. 3,855,638 (Pilliar) and 4,550,448 (Kenna), which are also incorporated herein by reference. Cementless prostheses are available commercially from numerous companies, including Zimmer, Inc., Warsaw, Ind.; Johnson & Johnson, New Brunswick, N.J.; and Dow Corning, Lexington Tenn.

The porous surface of the implants permits bone ingrowth into the device, providing for prosthesis fixation. The requirements for bone ingrowth into a porous surface include rigid internal fixation, proper pore size, usually between 250 and 400 microns, and intimate contact between the prosthesis and the host bone. If any of these requirements are not met; poor fixation is inevitable, usually with fibrous tissue ingrowth rather than bone.

There have been recent successful clinical trials with the use of cementless prosthesis for the hip and knee and many surgeons believe that this is the best surgical procedure for young patients where the durability of a cemented prosthesis is clearly in question. Additionally, cementless devices are almost always used in revision surgery.

Although techniques for implanting the cementless devices are known in the art, these techniques are not without disadvantages. The primary problem with the use of cementless devices in a human bone is achieving rigid fixation and intimate contact between the device and host bone. The device is typically press fit into the prepared bone surfaces, either the medullary canal of the femur and acetabulum (in hip arthoplasty) or the surfaces of the distal femur and proximal tibia (in total knee arthroplasty). The fit needs to be so tight and exact that fracture of bone during insertion is not an uncommon occurrence.

A second problem encountered is the wide variation in the size and shape of human bone. Despite the available selection of sizes of these prostheses, it is impossible to perfectly fit the prosthesis to the host bone.

A further problem is in the bone preparation, even with the most precise surgical cuts and techniques, microscopic gaps between the host bone and the prosthesis are inevitable, making bone ingrowth unpredictable. This problem is of particular concern in revision surgery. After each arthroplasty, marked bone loss occurs creating large holes where it is exceedingly difficult to achieve fixation and intimate contact between the porous surface and the host bone. In revision surgery bone ingrowth into the porous surface is very unpredictable.

It is therefore desirable to eliminate gaps between the prosthesis and the host bone. A method of eliminating this gap, thus providing for intimate contact would be advantageous for bone ingrowth. Selection of the appropriate material to fill the gap is critical to the success of such a method. The most desirable material would be one that temporarily fills the gap, provides for initial fixation, is osteoconductive, and is bioresorbable, allowing bone to replace this material. In addition, it must be well tolerated by the host.

A material that can be used in the operating room that has similar properties to methyl methacrylate is also desirable. Methyl methacrylate goes through stages of first being free-flowing, then doughy and finally polymerizes into a hardened material. Such a material will in effect result in a biologic bone scaffold or interface which can be used, for example, in conjunction with a cementless hip without any change in the surgical technique, other than the use of the interface prior to seating the device.

Finally, the material needs to have a controlled rate of both hardening and resorbtion such that it will harden in the operating room short of 10 minutes, and will last a minimum of four weeks in the host to achieve prosthesis fixation.

While the prior art discloses the use of a bioresorbable material for use in bone implantations and prosthesis parts, there has been no suitable solution to the gap-filling problem described above. Most of the materials which have been tested are either inorganic or organic polymers, many of which are used in the dental industry.

For example, U.S. Pat. No. 4,619,655 (Hanker et al.) discloses prostheses for bone repair or reconstruction which are comprised of plaster of Paris mixed with a non-bioresorbable calcium particles. The plaster of Paris functions as a biodegradable scaffold or binder to hold the non-bioresorbable calcium particles together. This patent teaches that the plaster of Paris is absorbed and replaced simultaneously by fibrovascular tissue which in turn is replaced by bone. The prostheses are, however, comprised of the mixture of the non-bioresorbable calcium particles, with the plaster of Paris merely holding the particles together. The mechanical strength of the calcium particle matrix after the plaster of Paris has been resorbed may be unsatisfactory for a prosthesis.

U.S. Pat. No. 4,356,572 (Guillemin et al.) discloses the use of calcium carbonate as a bone prosthesis part. According to one embodiment disclosed in this patent, a nonresorbable endoprosthetic element includes a hollow section which contains calcareous material. The endoprosthetic element is configured such that the hollow part communicates with the outside of the element. When the prosthesis is inserted, the communicating sections of the prosthesis are disposed such that they are in contact with bony substance. The calcium carbonate is progressively replaced by newly formed bone, forming an anchorage for the endoprosthetic element.

U.S. Pat. No. 4,309,488 (Heide et al.) discloses bone replacement materials that consist of a solid core of metal that is compatible with body tissue and a calcium phosphate ceramic material disposed on the peripheral areas of the core. The calcium phosphate ceramic material serves as an interface between the core and the bone tissue.

These prior art references, however, do not provide a solution to the problem of the unpredictability of the bone ingrowth in the gaps which result between the host bone and the prosthesis.

Some efforts have also been devoted to finding a more suitable bone cement. For example, U.S. Pat. No. 4,373,217 (Draenert) discloses the use of a resorbable tricalcium phosphate in a methyl methacrylate implantation material. The implantation material disclosed by this reference however suffers from the disadvantages described above with respect to the use of methyl methacrylate.

Therefore in view of the above it is a primary object of the present invention to provide a method of implanting a cementless prosthesis which will achieve rigid fixation of the prosthesis.

It is a further object of the present invention to provide a method of implanting a cementless prosthesis which will improve bone ingrowth in gaps which result between the prosthesis and the host bone.

It is a more specific object of the present invention to provide a method of implanting a prosthesis wherein gaps which result between the prosthesis and the host bone are initially filled to provide an initial fixation and wherein the filling material is subsequently replaced by bone tissue.

SUMMARY OF THE INVENTION

To achieve the foregoing and other objects of and in accordance with the purposes of the present invention an improved method for implanting a prosthesis is provided. According to this method, a prosthesis is implanted by preparing the host bone to receive the mating surface of the prosthesis, applying calcium sulfate in free-flowing form to the receiving surface of the host bone, and seating the prosthesis in the host bone whereby gaps which result between the prosthesis and the host bone are filled with the calcium sulfate.

After the calcium sulfate is allowed to harden, it provides rigid fixation of the prosthesis in the host bone. Since calcium sulfate is osteoconductive and bioresorbable, it will ultimately be resorbed by the body and replaced by bone tissue.

DETAILED DESCRIPTION OF THE PRESENTLY PREFERRED EMBODIMENTS

In the preferred embodiment of the present invention, a prosthesis is implanted into a host bone using a novel surgical procedure which encourages bone growth in the gaps which result between the prosthesis and the host bone.

Using techniques conventionally known in the art, an incision in the skin and muscle is made in the area proximate to the host bone. After the incision has been made, again using techniques known in the art, the host bone is prepared to receive the prosthesis by preparing the receiving surface of the host bone to mate with the respective engaging surface of the prosthesis. For example, in hip arthoplasty, a cavity is formed in the host bone where the prosthesis is to be installed. A suitable prosthesis is then selected. Preferably, the prosthesis has a porous surface as described above and is of a size and configuration that fits tightly into the host bone. The tight fit assures that the gaps which result between the prosthesis and the host bone are minimized. The host bone/prosthesis interface material, in free-flowing form, is applied to the receiving surface of the host bone. The prosthesis is than inserted into the receiving cavity. Gaps which result between the prosthesis and the host bone are filled with the bone/prosthesis interface which is described in more detail hereinafter. Using the bone/prosthesis interface in free-flowing form facilitates the application of the interface during the installation procedure. After the prosthesis has been installed, the bone/prosthesis interface is allowed to harden, and the incision is closed using known techniques.

The bone/prosthesis interface material in free-flowing form may be applied using any suitable technique. Preferably, the interface is applied to the receiving surface of the host bone before the prosthesis is inserted using a conventional cement syringe of the type used for methyl methacrylate. Less preferably, the interface may be applied by injecting it into the gaps after the prosthesis has been inserted into the cavity.

It has been discovered that calcium sulfate hemihydrate ($CaSO_4 \cdot \frac{1}{2} H_2O$), such as a medical grade calcium sulfate hemihydrate, available from U.S. Gypsum Corporation (Chicago, Ill.), has all of the above-mentioned desirable properties for a bone/prosthesis interface.

Calcium sulfate, also known as plaster of Paris, is a material which has been previously used in orthopedics. The hemihydrate starts out as a powder, and when mixed with water or saline solution will form a relatively free-flowing liquid, then go through a doughy state, and finally will go to a hardened state during a process of hydration.

The hardening rate and strength of calcium sulfate can be controlled by known methods. For example, the hardening rate may be accelerated by using saline solution instead of water. The strength of the hardened state, which depends on the density of the hardened state, can also be altered during the preparation process by known techniques.

Prior studies with the use of calcium sulfate have shown it to be bioresorbable, bio-compatible and osteoconductive. When implanted in drill holes in animals, it has been shown to resorb, filling the hole in a predictable manner with bone.

The calcium sulfate hemihydrate may be prepared for use in the procedure by known techniques. In the preferred composition, the properties of the calcium sulfate include: (1) the ability of the material to be easily taken up and delivered by a syringe when 100 parts of powder are mixed with 32 parts of water or saline and (2) when mixed at this consistency with 0.9 N saline, the material will harden in a time period of from about 5 to about 10 minutes. The calcium sulfate may be sterilized by suitable methods such as by subjecting it to ionizing radiation.

In a preferred embodiment, the calcium sulfate interface may be loaded with one or more antibiotics. For example, as is conventional with methyl methacrylate, one or more antibiotics may be mixed with the calcium sulfate in powdered form prior to mixing with water or saline solution. Alternatively, one or more antibiotics may be dissolved in the saline solution. This antibiotic impregnation of the interface provides a further advantage by providing a vehicle for applying antibiotics in cementless arthoplasty. Antibiotic loading as a method of local antibiotic therapy in bone infection was disclosed by Mackey et al. in "Antibiotic Loaded Plaster of Paris Pellets," Clinical Orthopedics and Related Research, 167, 263-268 (1982), which is incorporated herein by reference. This technique may be particularly useful in revision surgery where cementless prostheses are preferred.

EXAMPLE I

Surgical Procedure

Three adult dogs were used in the surgical procedures. Non-weight bearing prostheses designed for the canine were implanted in both humeri of each dog. The prostheses were made of a solid core rod of titanium alloy, titanium 6 aluminum 4 vanadium with a titanium fiber metal porous surface. The prostheses had polyethylene spacers to maintain a 3 mm gap between the prosthesis and the host bone. Under general anesthesia using sterile technique, the proximal humerus was exposed in the animals. A cylindrical cavity prepared within the medullary canal in the cancellous bone using a power drill at low speed. The prosthesis was centered within the cavity and maintained in this position by the polyethylene spacers. The calcium sulfate material was prepared in the operating room by mixing 50 grams of sterile radiated calcium sulfate hemhydrate with 7 cc of 0.9 N saline solution.

The material in free-flowing form was injected into the drilled hole of the left humerus. The free-flowing calcium sulfate material was injected around the previously implanted cementless prosthesis thus filling the gap between the prosthesis and host bone. The outermost polyethylene spacer was inserted and the wound closed in a known manner. The control was the opposite right humerus where a similar prosthesis was inserted without the calcium sulfate interface.

After the surgical procedure, x-rays were taken of the prosthesis in-situ on both the right and left humeri of the three dogs. The dogs were given narcotics for analgesia in the immediate post-operative period. The animals were allowed unrestricted use of their extremities and were fed a standard diet. The animals were sacrificed humanely. Radiographs were taken post-operatively as mentioned and at sacrifice.

Both humeri were removed at autopsy for histological examination. Undecalcified sections were prepared embedding the bone and prosthesis in methacrylate allowing the methacrylate to cure and then finally cutting the bone in transverse sections. The sections were ground and stained in a known manner for undecalcified histological examinations.

The specimens were examined histologically and compared. The findings indicated that there was proliferative woven bone formation in the calcium sulfate interface which filled the gap. Bone was found to bridge the gap to the fiber in virtually 95% of the circumference of the prosthesis. The bone appeared viable, without any evidence of foreign body reaction to the calcium sulfate. In fact only small residuals of calcium sulfate were visible in the animals at 4 weeks. There were no foreign body giant cells or other signs of adverse reaction. There was a significant amount of osteoplastic rimming of this woven bone in the gap. The bone penetrated the fiber all the way to the solid core of the prosthesis. There was no evidence of fibrous tissue ingrowth. This phenomenon of gap filling was present throughout the entire length of the prosthesis as demonstrated by the multiple sections. The control prosthesis in the animals on the other hand showed significant gap reservation. While there was 10% trabecular bone growth into the gap along the circumference of the prosthesis, 90% remained bone-free. There was little evidence of bone penetration into the fiber of the prosthesis. This lack of ingrowth and gap filling was characteristic of all of the control animals at four weeks.

This study indicates the efficacy of calcium sulfate as a gap filler and further indicates that its properties as an osteoconductive agent are acceptable for its role as a bone/prosthesis interface. The material was clearly bioresorbable without histological evidence of adverse reaction and enhanced bone ingrowth when compared to the control prosthesis in the animals.

EXAMPLE II

In a surgical procedure to replace the head or ball of the hip in a human patient, conventional techniques are used to remove the ball and neck of the femur. First, an incision is made through the skin and muscle in a manner known in the art. Next the hip is dislocated, the ball and neck removed, and a rasp is used to prepare a cavity in the host bone.

The calcium sulfate material is prepared by mixing 200 g of sterile calcium sufate hemyhydrate with 28 cc of 0.9 N saline solution to produce a free-flowing suspension. The suspension is then applied to the surface of the cavity using a conventional cement syringe of the type used for methyl methanylate. A prosthesis, having a porous surface and a size and configuration that fits tightly into the prepared surface, is then press fit into the cavity in the conventional manner for a cementless prosthesis. Any gaps which result between the prosthesis and the surface of the cavity are filled with the calcium sulfate interface, while the excess is expelled from the cavity upon insertion of the prosthesis. The calcium sulfate interface is allowed to harden, and the procedure is then completed in a known manner.

I claim:

1. A method of implanting a prosthesis in a host bone comprising the steps of:
    preparing the surface of the host bone to receive the respective engaging surface of the prosthesis, thereby defining mating surfaces;
    mixing a material consisting essentially of calcium sulfate hemihydrate with water to produce a free-flowing suspension;

applying the calcium sulfate suspension in free-flowing form to the receiving surface of the host bone; and seating the prosthesis in the host bone such that the mating surfaces of the prosthesis and the host bone engage, whereby one or more cavities which result between the mating surfaces of the prosthesis and a host bone are filled with the calcium sulfate.

2. The method of claim 1 wherein the water further includes dissolved sodium chloride.

3. The method of claim 2 wherein the sodium chloride is present in an amount to produce a 0.9 N saline solution.

4. The method of claim 1 wherein the calcium sulfate hardens in a time period of from about 5 to about 10 minutes.

5. The method of claim 1 further comprising the step of:

mixing at least one antibiotic with the calcium sulfate to provide an antibiotic-loaded calcium sulfate interface.

6. The method of claim 5 wherein the step of mixing at least one antibiotic with the calcium sulfate comprises:

mixing at least one antibiotic with the calcium sulfate in powdered form to provide an antibiotic-loaded mixture; and mixing the antibiotic-loaded mixture with water.

7. The method of claim 5 wherein the step of mixing at least one antibiotic with the calcium sulfate comprises:

dissolving at least one antibiotic in water; and mixing the calcium sulfate hemihydrate with the water having the dissolved antibiotic.

8. The method of claim 1 wherein the prosthesis is a hip prosthesis.

9. The method of claim 1 wherein the prosthesis is a knee prosthesis.

* * * * *